United States Patent [19]
Kjell

[11] Patent Number: 5,955,608
[45] Date of Patent: *Sep. 21, 1999

[54] PROCESS FOR PREPARING BENZOIC ACID DERIVATIVE INTERMEDIATES AND BENZOTHIOPHENE PHARMACEUTICAL AGENTS

[75] Inventor: Douglas P. Kjell, West Lafayette, Ind.

[73] Assignee: Eli Lilly and Company, Indianapolis, Ind.

[ * ] Notice: This patent is subject to a terminal disclaimer.

[21] Appl. No.: 09/016,761

[22] Filed: Jan. 30, 1998

Related U.S. Application Data

[62] Division of application No. 08/298,891, Aug. 31, 1994, Pat. No. 5,731,436.

[51] Int. Cl.$^6$ ...................... C07D 265/30; C07D 211/08; C07D 211/34; C07D 207/04
[52] U.S. Cl. .......................... 544/172; 546/192; 546/238; 546/342; 548/572
[58] Field of Search ............................. 544/172; 546/192, 546/238, 342; 548/572

[56] References Cited

U.S. PATENT DOCUMENTS

| | | | |
|---|---|---|---|
| 4,133,814 | 1/1979 | Jones et al. | 260/326.5 |
| 4,380,635 | 4/1983 | Petera | 546/202 |
| 4,418,068 | 11/1983 | Jones | 424/267 |
| 5,731,436 | 3/1998 | Kjell | 544/172 |

OTHER PUBLICATIONS

Yoshino, T., et al., *Bulletin of the Chemical Society of Japan*, 46:553–556 (1973).
Carlson, W. W., et al., *J. Am. Chem. Soc.* 69:1952–1956 (1947).
Jones, et. al. *J. Med. Chem.*, 27, No. 8, 1057–1066, (1984).

*Primary Examiner*—John Kight
*Assistant Examiner*—Raymond Covington
*Attorney, Agent, or Firm*—Gilbert T. Voy

[57] ABSTRACT

Novel processes for producing benzothiophenes employing ethylene carbonate or propylene carbonate are provided.

15 Claims, No Drawings

PROCESS FOR PREPARING BENZOIC ACID DERIVATIVE INTERMEDIATES AND BENZOTHIOPHENE PHARMACEUTICAL AGENTS

This application is a division of Ser. No. 08/298,891 filed Aug. 31, 1994 now U.S. Pat. No. 5,731,436.

FIELD OF THE INVENTION

The present invention relates to the fields of pharmaceutical and organic chemistry and provides novel processes for preparing compounds of formula I

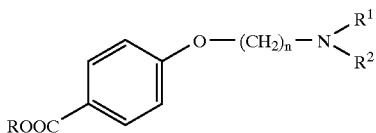

wherein
R is $C_1$–$C_4$ alkyl;
$R^1$ and $R^2$ each are independently $C_1$–$C_4$ alkyl, or combine to form piperidinyl, pyrrolidinyl, methylpyrrolidinyl, dimethylpyrrolidinyl, morpholino, dimethylamino, diethylamino, or 1-hexamethyleneimino; and
n is 2 or 3;
or a pharmaceutically acceptable salt thereof; and compounds of formula II

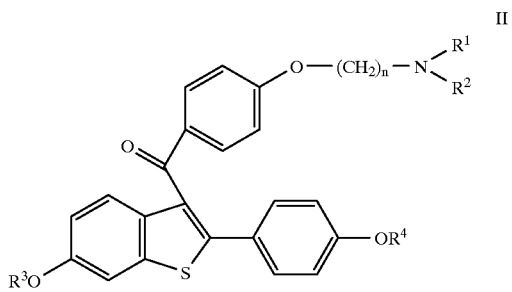

wherein
$R^3$ and $R^4$ each are H or a hydroxy protecting group; and
$R^1$, $R^2$, and n are as defined above;
or a pharmaceutically acceptable salt thereof.

Compounds of formula II, particularly raloxifene, in which $R^1$ and $R^2$ combine to form a piperidinyl moiety, $R^3$ and $R^4$ each are H, and n is 2, are well known in the pharmaceutical art as having activity for the treatment of certain disease states including, for example, osteoporosis.

BACKGROUND OF THE INVENTION

Typically, compounds of formula I are prepared by reacting, for example, b-chloroethylpiperidine hydrochloride and ethyl 4-hydroxybenzoate in methyl ethyl ketone, in the presence of potassium carbonate (see, U.S. Pat. No. 4,418,068.) However, the referenced synthetic route has certain undesirable aspects. Firstly, the solvent, methyl ethyl ketone, is hazardous and requires expensive handling and disposal procedures. Secondly, use of this solvent sets a limit of 80° C. as a reaction temperature during formation of an ester, thus limiting the rate of the potassium carbonate catalyzed alkylation reaction. Furthermore, the organic layer containing the ester must be stripped to an oil prior to dissolution of the oil in aqueous sodium hydroxide and methanol. This oil preparation step is time consuming and could reduce the ultimate yield with large-scale production.

Thus, a more efficient, less expensive process for preparing compounds of formula I, and, ultimately, compounds of formula II, especially if such an efficient process did not require the use of hazardous solvents, would be a significant and desirable advance over the current state of the art. The present invention provides such a process.

Analogously, Yoshino, et al., *Bulletin of the Chemical Society of Japan,* 46:553–556 (1973), disclose condensation reactions of ethylene carbonate with a variety of phenols in the presence of tetraethylammonium halides or a metal hydride such as lithium or sodium hydride. These reactions generally are run in the presence of dimethylformamide (DMF) as a solvent, the presence of which creates considerable limitations. Most importantly, the use of DMF would require the isolation of each intermediate compound prepared by the process of the present invention prior to the commencement of the subsequent step. The replacement of DMF with a solvent which would allow each step of the present processes to be run without isolating each intermediate would provide a significant advance to the present state of the art. Such an advance is provided by the present processes.

SUMMARY OF THE INVENTION

The present invention provides a novel process for preparing compounds of formula I

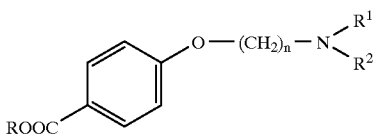

wherein
R is $C_1$–$C_4$ alkyl;
$R^1$ and $R^2$ each are independently $C_1$–$C_4$ alkyl, or combine to form piperidinyl, pyrrolidinyl, methylpyrrolidino, dimethylpyrrolidino, morpholino, dimethylamino, diethylamino, or 1-hexamethyleneimino; and
n is 2 or 3;
or a pharmaceutically acceptable salt thereof, comprising a) condensing ($C_1$–$C_4$ alkyl) 4-hydroxybenzoate with ethylene carbonate or propylene carbonate in the presence of a condensation catalyst and a moderately polar, water immiscible solvent having a high boiling point;

b) reacting the product of step a), a compound of formula III

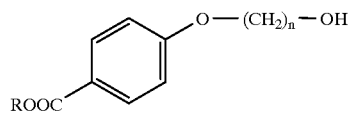

wherein
R and n are as defined above, with a leaving group donor; and c) reacting the product of step b), a compound of formula IV

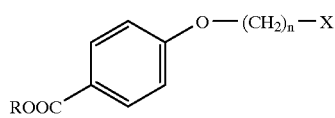

IV wherein
R and n are as defined above; and
X is a leaving group, with a base selected from the group consisting of piperdine, pyrrolidine, methylpyrrolidine, dimethylpyrrolidine, morpholine, dimethylamine, diethylamine, and 1-hexamethyleneimine.

The present invention also provides a novel process for preparing compounds of formula II

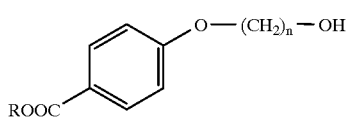

II wherein
R is $C_1$–$C_4$ alkyl;
$R^1$ and $R^2$ each are independently $C_1$–$C_4$ alkyl, or combine to form piperidinyl, pyrrolidinyl, methylpyrrolidino, dimethylpyrrolidino, morpholino, dimethylamino, diethylamino, or 1-hexamethyleneimino; and
n is 2 or 3;
or a pharmaceutically acceptable salt thereof, comprising
a) condensing ($C_1$–$C_4$ alkyl) 4-hydroxybenzoate with ethylene carbonate or propylene carbonate in the presence of a condensation catalyst and a moderately polar, water immiscible solvent having a high boiling point;
b) reacting the product of step a), a compound of formula III

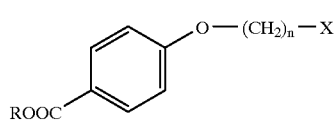

III wherein
R and n are as defined above, with a leaving group donor;
c) reacting the product of step b), a compound of formula IV

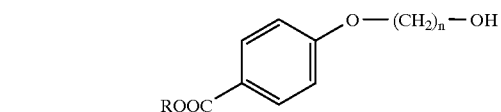

IV wherein
R and n are as defined above; and
X is a leaving group, with a base selected from the group consisting of piperdine, pyrrolidine, methylpyrrolidine, dimethylpyrrolidine, morpholine, dimethylamine, diethylamine, and 1-hexamethyleneimine;

d) reacting the product of step c) with a compound of formula IV

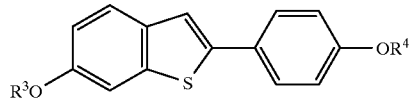

V wherein $R^3$ and $R^4$ are as defined above, or a pharmaceutically acceptable salt thereof;
e) optionally removing the hydroxy protecting groups from the reaction product from step d); and
f) optionally forming a salt of the reaction product from either step d) or step e).

Further provided are novel compounds of formula I above, which are useful as intermediates for preparing compounds of formula II above.

DETAILED DESCRIPTION OF THE INVENTION

One aspect of the present invention provides a process for preparing a compound of formula I

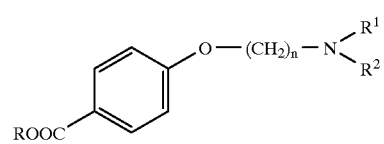

I wherein
R is $C_1$–$C_4$ alkyl;
$R^1$ and $R^2$ each are independently $C_1$–$C_4$ alkyl, or combine to form piperidinyl, pyrrolidinyl, methylpyrrolidino, dimethylpyrrolidino, morpholino, dimethylamino, diethylamino, or 1-hexamethyleneimino; and
n is 2 or 3;
or a pharmaceutically acceptable salt thereof, comprising
a) condensing ($C_1$–$C_4$ alkyl) 4-hydroxybenzoate with ethylene carbonate or propylene carbonate in the presence of a condensation catalyst and a moderately polar, water immiscible solvent having a high boiling point;
b) reacting the product of step a), a compound of formula III

III wherein
R and n are as defined above, with a leaving group donor; and
c) reacting the product of step b), a compound of formula IV

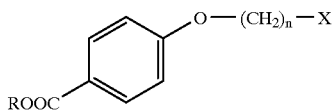

wherein

R and n are as defined above; and

X is a leaving group, with a base selected from the group consisting of piperidine, pyrrolidine, methylpyrrolidine, dimethylpyrrolidine, morpholine, dimethylamine, diethylamine, and 1-hexamethyleneimine.

General terms used in description of chemical formulae herein bear their usual meanings. For example, the term "$C_1$–$C_4$ alkyl" refers to straight or branched chains of 1 to 4 carbon atoms including, methyl, ethyl, propyl, isopropyl, butyl, n-butyl, and isobutyl.

The term "halo" includes bromo, chloro, fluoro, and iodo.

In formula II compounds, the $R^3$ and $R^4$ hydroxy protecting groups, when $R^3$ and $R^4$ are not H, denote groups which generally are not found in final, therapeutically active compounds, but which are intentionally introduced during a portion of the synthetic process to protect a group which otherwise might react in the course of chemical manipulations, and is then removed at a later stage of the synthesis. Since compounds bearing such protecting groups are of importance primarily as chemical intermediates (although some derivatives also exhibit biological activity), their precise structure is not critical. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley (New York, 1981); and *The Peptides*, Vol. I, Schrooder and Lubke, Academic Press (London and New York, 1965).

Representative hydroxy protecting groups include, for example —$C_1$–$C_4$ alkyl, —CO—($C_1$–$C_6$ alkyl), —$SO_2$—($C_4$–$C_6$ alkyl), and —CO—Ar in which Ar is optionally substituted phenyl. The term "substituted phenyl" refers to a phenyl group having one or more substituents selected from the group consisting of $C_1$–$C_4$ alkyl, $C_1$–$C_5$ alkoxy, hydroxy, nitro, chloro, fluoro, and tri(chloro or fluoro) methyl. The term "$C_1$–$C_5$ alkoxy" represents a $C_1$–$C_5$ alkyl group attached through an oxygen bridge such as, for example, methoxy, ethoxy, n-propoxy, isopropoxy, and the like. Preferred $R^3$ and R4 hydroxy protecting groups are $C_1$–$C_4$ alkyl, particularly methyl.

In the present, novel process ($C_1$–$C_4$ alkyl) 4-hydroxybenzoate is condensed with ethylene carbonate or propylene carbonate, preferably the former, in the presence of an appropriate condensation catalyst and a moderately polar, water immiscible solvent having a high boiling point. Each of the starting materials used in the first step of the present process [step a)] are commercially available or can be prepared via procedures well known to the skilled artisan.

The amount of reactants used in this reaction is that amount necessary to affect coupling. Typically, an equivalent amount to, preferably, a slight excess of the ethylene carbonate or propylene carbonate is used for each equivalent of ($C_1$–$C_4$ alkyl) 4-hydroxybenzoate, preferably ethyl 4-hydroxybenzoate, substrate.

Appropriate condensation catalysts include tetra($C_1$–$C_4$ alkyl)ammonium halides and metal hydrides such as, for example, lithium hydride. Preferably, an equivalent of ($C_1$–$C_4$ alkyl) 4-hydroxybenzoate substrate.

The solvent employed in the present reaction is a moderately polar, water immiscible solvent having a high boiling point. The term "moderately polar" means a solvent having a functional ester, ether, or halogen moiety and include, for example, amyl acetate, diethoxyethane, chlorobenzene, methyl benzoate, and anisole. Of these, anisole is especially preferred. The term "having a high boiling point" means those moderately polar, water immiscible solvents which have boiling points greater than 100° C. Because the present reaction step, and each reaction step of the present process can be run at temperatures in the range from about a minimum of 100° C. to reflux of the given reaction mixture, the upper temperature limit of the selected solvent is unlimited, provided the solvents boiling point is greater than 100° C. However, when anisole, the preferred solvent, is employed, it is preferred to run the first step of the present reaction in the temperature range from about 130° C. to about 150° C.

The solvents used in the present process provide distinct advantages over the prior art ketone and highly polar solvents such as DMF. Compared to ketone solvents such as methyl ethylketone, the solvents used in the present process require less expensive handling and disposal procedures. Equally important, the solvents used in the present process allow the process steps to be run at a higher temperature than the solvents disclosed in the prior art. Furthermore, when compared to highly polar solvents such as DMF, the solvents of the present process allow each step of the process to be run without isolating each intermediate. Thus, the solvents used in the present process provide a distinct and unexpected advantage over the solvents discussed in the prior art for analogous reactions.

The length of time for this reaction to run is that amount necessary for the desired intermediate to be prepared. Typically, the first reaction step of the present process takes from about 15 hours to about 60 hours. The optimal time can be determined by monitoring the progress of the reaction via conventional chromatographic techniques such as thin layer chromatography.

In addition, it is preferred to maintain each reaction step of the present process under an inert atmosphere such as, for example, argon, or, particularly, nitrogen.

The first step of the present process provides a compound of formula III

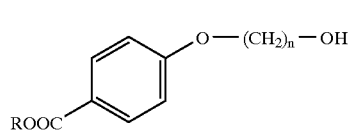

wherein R and n are as defined above, which then is reacted with a leaving group donor via well known procedures. Typically, the hydrogen of the hydroxy moiety of a formula III compound, in which R preferably is ethyl, is substituted with a leaving group such as, for example, a sulfonate such as methanesulfonate, 4-bromobenzenesulfonate, toluenesulfonate, ethanesulfonate, isopropanesulfonate, 4-methoxybenzenesulfonate, 4-nitrobenzenesulfonate, 2-chlorobenzenesulfonate, triflate, and the like, halogens such as iodo or bromo, and other related leaving groups. A leaving group donor, therefore, is a compound which will substitute a formula III compound with a leaving group to provide a compound of formula IV

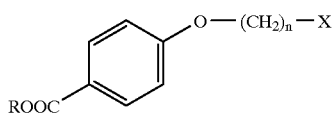

wherein X is a leaving group.

For the present reaction step, an equivalent to, preferably, a slight excess of a leaving group donor, preferably sulfonyl chloride, is used for each equivalent of a formula III compound. The reaction generally is run in the presence of an appropriate base, such as pyridine, under an inert atmosphere.

The present reaction may be run at a temperature from about 60° C. to about 90° C., preferably, at about 75° C., and is run in a relatively short period of time; typically from about one-half hour to two hours. Of course, conventional chromatographic techniques may be used to determine the progress of the reaction. Additional compounds of formula IV may be provided by allowing the reaction mixture to sit for about another 6 to about 18 hours after the above-heating period, adding about one-half equivalent of the desired leaving group donor per each equivalent of formula III substrate, heating for about one-half hour to about two hours, and allowing the mixture to cool to ambient temperature.

In the third step of the present process, a compound of formula IV above is reacted with at least 2 equivalents of a base selected from the group consisting of piperidine, pyrrolidine, methylpyrrolidine, dimethylpyrrolidine, morpholine, dimethylamine, diethylamine, or 1-hexamethyleneimine per equivalent of a formula IV compound, in the presence of an appropriate base, via well known procedures.

Appropriate bases include organic and inorganic bases, but inorganic bases, particularly a carbonate or bicarbonate base, is preferred. Of these, powdered potassium carbonate is especially preferred.

Furthermore, it is preferred to maintain the present reaction step under an inert atmosphere such as, for example, argon or, particularly, nitrogen.

The present reaction may be run at a temperature from about 60° C. to about 100° C. Preferably, this reaction is run at about 80° C.

Typically, this reaction is run in from about 2 to about 18 hours, and the progress of the reaction can be monitored using standard chromatographic techniques.

The product of the present process is isolated and purified via procedures well known to one of ordinary skill in the art, particularly as hereinafter described.

The reaction products from steps a) and b) of the present process may be isolated and purified, via standard techniques, prior to commencement of the next step of the present process, or, preferably, each step, a), b), and c), is run in the same vessel.

The product of the present process, a compound of formula I, is novel and useful as an intermediate for preparing pharmaceutically active compounds of formula II.

Another aspect of the present invention provides a process for preparing a compound of formula II

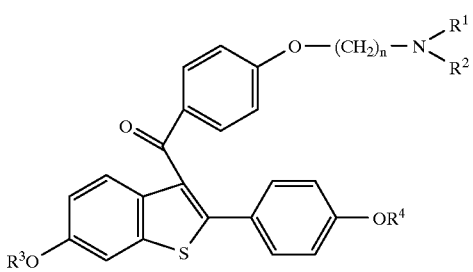

wherein
R is $C_1$–$C_4$ alkyl;
$R^1$ and $R^2$ each are independently $C_1$–$C_4$ alkyl, or combine to form piperidinyl, pyrrolidinyl, methylpyrrolidino, dimethylpyrrolidino, morpholino, dimethylamino, diethylamino, or 1-hexamethyleneimino; and
n is 2 or 3;
or a pharmaceutically acceptable salt thereof, comprising
a) condensing ($C_1$–$C_4$ alkyl) 4-hydroxybenzoate with ethylene carbonate or propylene carbonate in the presence of a condensation catalyst and a moderately polar, water immiscible solvent having a high boiling point;
b) reacting the product of step a), a compound of formula III

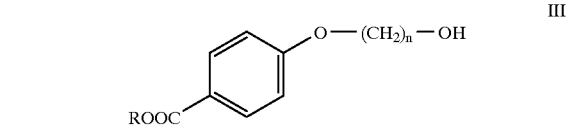

wherein
R and n are is as defined above, with a leaving group donor;
c) reacting the product of step b), a compound of formula IV

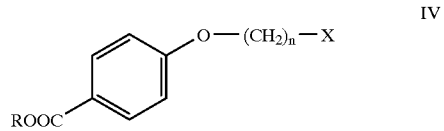

wherein
R and n are as defined above; and
X is a leaving group, with a base selected from the group consisting of piperidine, pyrrolidine, methylpyrrolidine, dimethylpyrrolidine, morpholine, dimethylamine, diethylamine, and 1-hexamethyleneimine;
d) reacting the product of step c) with a compound of formula V

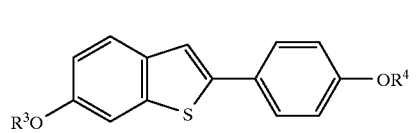

wherein $R^3$ and $R^4$ are as defined above, or a pharmaceutically acceptable salt thereof;
e) optionally removing the reaction product from step d); and f) optionally forming a salt of the reaction product from either step d) or step e).

For the present, novel process, steps a), b), and c) are the same as steps a), b), and c) in the above described process, plus additional steps d) (acylation of formula V compound with a formula I compound), step e) (optional removal of any hydroxy protecting group), and step f) (optional salt formation of a protected or deprotected compound of formula II).

In step d), the reaction product from step c) which, preferably, is isolated and purified prior to the initiation of this step, is reacted with a compound of formula V

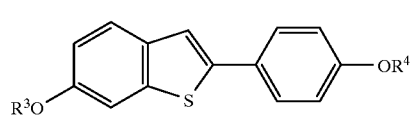

V wherein $R^3$ and $R^4$ are as defined above.

Compounds of formula V, are known in the art and are prepared, for example, as described by Peters in U.S. Pat. No. 4,380,635, or Jones, et al., in U.S. Pat. Nos. 4,133,814 and 4,418,068, each of which is herein incorporated by reference. Although the $R^3$ and $R^4$ protecting groups are not required for this step, thus allowing a compound of formula V in which $R^3$ and $R^4$ are hydrogen to be acylated with a compound of formula I in which $R^3$ and $R^4$ each are hydrogen, one skilled in the art would recognize that a hydroxy protecting group, particularly methyl, would be preferred. A preferred formula I compound for one present acylation reaction is that in which $R^1$ and $R^2$ are combined to form piperidinyl and n is 2.

Reagents and all parameters necessary to carry out the acylation step of step d), the optional deprotection step of step e), the optional salt formation step of step f), and isolation and purification of formula II compounds are described in the afore-incorporated United States patents. Thus, pharmaceutically active compounds of formula V, including their acid addition salts, are prepared via the instant process of the present invention.

The following examples are provided for the purpose of illustrating the present invention and are not intended to be limiting upon the scope of the invention.

EXAMPLE 1

Ethyl 4-(2-piperidinoethoxy)benzoate

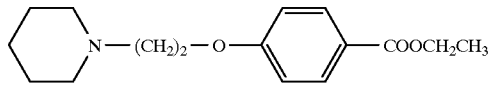

To a 250 mL 3 neck flask with mechanical stirring, condenser, and a resistant thermal device (RTD probe) connected via temperature controller to a heating mantle and under nitrogen atmosphere are added: 8.31 g of ethyl 4-hydroxybenzoate, 4.84 g of ethylene carbonate, 0.05 g of tetrabutylammonium iodide, and 60 mL of anisole. The mixture was heated to 140° C. for about 48 hours. Thin layer chromatography (conducted in an ethyl acetate solvent system) revealed the presence of only a small amount of starting material.

To 11 mL of the resulting solution (containing about 10.0 mmol of ethyl 4-(2-hydroxyethoxy)benzoate) was added 1.78 mL (22 mmol) of pyridine and 0.85 mL (11 mmol) of methane sulfonyl chloride under nitrogen. The mixture was heated to 75° C. for 24 hours. An additional 0.04 mL (5 mmol) of methane sulfonyl chloride was then added and heating was continued. After 1 hour, the mixture was cooled to ambient temperature and 10 mL of water was added followed by the addition of 10 mL of ethyl acetate. The layers were separated and the aqueous layer discarded. NMR analysis revealed that the organic layer contained ethyl 4-(2-methanesulfonylethoxy)benzoate.

To a 25 mL round bottom flask with magnetic stirring and condenser and under nitrogen were added the following: the solution from step 2 containing about 10.0 mmol of ethyl 4-(2-methanesulfonylethoxy)benzoate, 2 mL (20 mmol) of piperidine, and 1.5 g $K_2CO_3$. The mixture was heated to 80° C. for 24 hours and then to 125° C. for an additional 24 hours to yield product. The yield was estimated to exceed 90%. The product was identical by chromatography and $^1$H-NMR to that found by published methods.

EXAMPLE 2

Methyl (2-piperidinoethoxy)benzoate

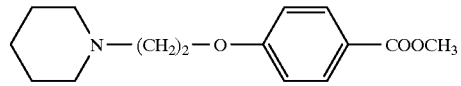

To a 250 mL round bottom flask with magnetic stirring and a condenser, under nitrogen atmosphere were added the following: 7.61 g of (0.05 mol) methyl 4-hydroxybenzoate, 5.32 g of (0.06 mol) ethylene carbonate, 0.05 g (1.4 mmol) of tetrabutylammonium iodide, and 60 mL of anisole. The mixture was heated to 147° C. for about 48 hours. After the flask was cooled to ambient temperature, the following were added: 8.9 mL (0.11 mol) and 6.25 mL (0.08 mol) methane sulfonyl chloride. The resulting mixture was heated to 75° C. for 20 hours and 100 mL of ethyl acetate was added. The mixture was washed twice with 100 mL aliquots of water and then dried over magnesium sulfate.

The flask contents were transferred to a 250 mL, 3 neck flask with mechanical stirring, condenser, and RTD probe hooked through a temperature controller to a heating mantle. 7.5 g of potassium carbonate and 10 mL (100 mmol) of piperidine were added. The reaction was heated to about 85° C. for about 5 days, and the resulting mixture was then quenched with water, and ethyl acetate was added until two distinct layers appeared. The aqueous layer was separated and discarded and the organic layer was washed twice with brine. The resulting organic layer was dried over magnesium sulfate and the solvent was removed under reduced pressure, yielding a solution of the title product in anisole. $^1$H-NMR chromatography confirmed the presence of the desired product. The yeild was grater than 95% of theory.

EXAMPLE 3

Ethyl 4-(2-piperidinoethoxy)benzoic acid hydrochloride

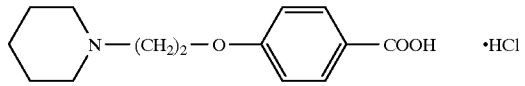

To the product solution from Example 1 is added 25 mL of 8N hydrochloric acid, and the resulting layers are separated. The aqueous acid layer is then heated to between 95° C. and reflux for about 4 hours to about 24 hours. The solution is cooled to about 0° C. to 5° C. and the crystalline product is collected by filtration and dried.

EXAMPLE 4

6-Hydroxy-2-(4-hydroxyphenyl)-3-[4-(2-piperidinoethoxy)benzyl]benzo[b]thiophene hydrochloride

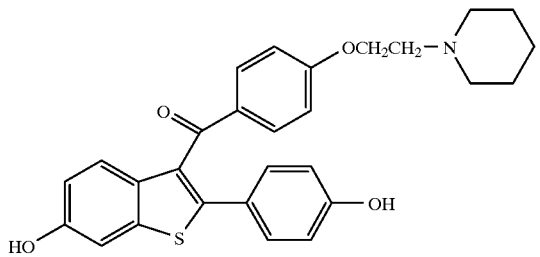

Under nitrogen atmosphere, a mixture of 3 g of ethyl 4-(2-piperidinoethoxy)benzoic acid hydrochloride, 2 drops of dimethylformamide, 2.5 mL of thionyl chloride, and 40 mL of chlorobenzene is heated to about 70° C. for about one hour. The excess thionyl chloride and about 15 mL to about 20 mL of solvent are then distilled off. The remaining suspension is cooled to ambient temperature and to it are added 100 mL of dichloromethane, 2.7 g of 6-methoxy-2-(4-methoxyphenyl-benzo[b]thiophene (as prepared via the procedures described in the above incorporated U.S. patents), and 10 g of aluminum chloride. The solution is stirred for about 1 hour, 7.5 mL of ethanethiol is added, and the mixture is stirred for an additional 45 minutes. Then 40 mL of tetrahydrofuran is added, followed by 15 mL of 20% hydrochloric acid, and heated to reflux. 50 mL of water and 25 mL of saturated aqueous sodium chloride are added. The mixture is stirred and allowed to cool to ambient temperature. The precipitate is collected by filtration and washed successively with 30 mL of water, 40 mL of 25% aqueous tetrahydrofuran, and again with 35 mL of water. The solids are then dried at 40° C., under vacuum, to obtain the title product.

We claim:

1. A process for preparing a compound of formula II

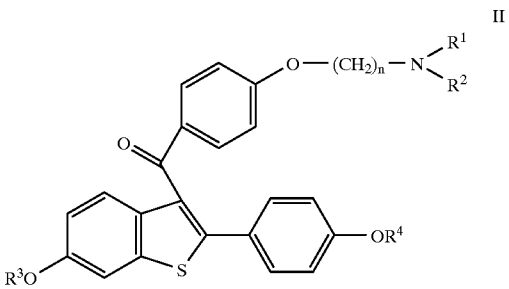

wherein

R is $C_1$–$C_4$ alkyl;

$R^1$ and $R^2$ each are independently $C_1$–$C_4$ alkyl, or combine to form piperidinyl, pyrrolidinyl, methylpyrrolidino, dimethylpyrrolidino, morpholino, dimethylamino, diethylamino, or 1-hexamethyleneimino; and n is 2 or 3;

or a pharmaceutically acceptable salt thereof, comprising a) condensing ($C_1$–$C_4$ alkyl) 4-hydroxybenzoate with ethylene carbonate or propylene carbonate in the presence of a condensation catalyst and a moderately polar, water immiscible solvent having a high boiling point;

b) reacting the product of step a), a compound of formula III

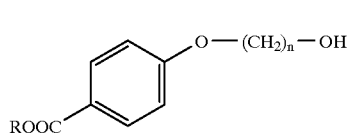

wherein

R and n are as defined above, with a leaving group donor;

c) reacting the product of step b), a compound of formula IV

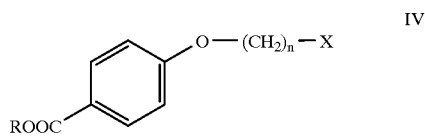

wherein

R and n are as defined above; and

X is a leaving group, with a base selected from the group consisting of piperidine, pyrrolidine, methylpyrrolidine, dimethylpyrrolidine, morpholine, dimethylamine, diethylamine, and 1-hexamethyleneimine;

d) reacting the product of step c) with a compound of formula IV

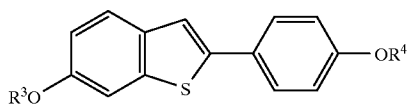

wherein R³ and R⁴ are as defined above, or a pharmaceutically acceptable salt thereof;

e) optionally removing the reaction product from step d); and f) optionally forming a salt of the reaction product from either step d) or step e).

2. A process according to claim 1 wherein n of said formula II compound is 2.

3. A process according to claim 2 wherein R¹ and R² of said formula II compound combine to form piperidinyl.

4. A process according to claim 3 wherein R³ and R⁴ of said formula II compound each are H.

5. A process according to claim 4 wherein said leaving group donor is sulfonyl chloride.

6. A process according to claim 5 wherein said ethylene or propylene carbonate is ethylene carbonate.

7. A process according to claim 6 wherein said solvent is anisole.

8. A process according to claim 7 wherein said pharmaceutically acceptable salt is the hydrochloride salt.

9. A process according to claim 8 wherein said steps a), b), and c) are run in a single vessel.

10. A process according to claim 3 wherein R³ and R⁴ of said formula II compound each are methyl.

11. A process according to claim 10 wherein said leaving group donor is sulfonyl chloride.

12. A process according to claim 11 wherein said ethylene or propylene carbonate is ethylene carbonate.

13. A process according to claim 12 wherein said solvent is anisole.

14. A process according to claim 13 wherein said pharmaceutically acceptable salt is the hydrochloride salt.

15. A process according to claim 14 wherein said steps a), b), and c), are run in the same vessel.

* * * * *